United States Patent [19]

Ellis

[11] Patent Number: 4,667,680

[45] Date of Patent: May 26, 1987

[54] APPARATUS AND METHOD FOR REDUCTION IN RESPIRATION ARTIFACT IN PULMONARY ARTERY PRESSURE MEASUREMENT

[75] Inventor: David M. Ellis, Bedford, Mass.

[73] Assignee: Hewlett-Packard Company, Palo Alto, Calif.

[21] Appl. No.: 551,221

[22] Filed: Nov. 14, 1983

[51] Int. Cl.[4] .............................................. A61B 5/02
[52] U.S. Cl. .................................... 128/672; 128/687
[58] Field of Search ............................... 128/670–672, 128/680–683

[56] References Cited

U.S. PATENT DOCUMENTS

| 4,140,110 | 2/1979 | Jansen et al. | 128/681 |
| 4,190,886 | 2/1980 | Sherman | 128/681 X |
| 4,223,681 | 9/1980 | Sherman | 128/672 |

FOREIGN PATENT DOCUMENTS 0140201 2/1980 Fed. Rep. of Germany ...... 128/671

Primary Examiner—Kyle L. Howell
Assistant Examiner—Angela D. Sykes
Attorney, Agent, or Firm—Donald N. Timbie

[57] ABSTRACT

Apparatus is disclosed for deriving weighted values $\overline{S}_i$, $\overline{D}_i$ and $\overline{M}_i$ to respectively represent the systolic, diastolic and mean blood pressures for each heartbeat of a patient from the values $S_i$, $D_i$ and $M_i$ that are the maximum, minimum and means blood pressures of the current heartbead; $S_{i-1}$, $D_{i-1}$ and $M_{i-1}$ that were the maximum, minimum and mean blood pressures for the previous heartbeat; $\overline{S}_{i-1}$, $\overline{D}_{i-1}$ and $\overline{M}_{i-1}$ that respectively represented the systolic, diastolic and means blood pressures of the previous heartbeat; and a constant $K_i$ that is a function, F, of the difference between $M_i$ and the mean pressure $M_{i-1}$ of the previous heartbeat. The expressions for $S_i$, $D_i$, $M_i$ and $K_i$ are as follows:

$$\overline{S}_i = \overline{S}_{i-1} + \frac{(S_i) - (\overline{S}_{i-1})}{K_i}$$

$$\overline{D}_i = \overline{D}_{i-1} + \frac{(D_i) - (\overline{D}_{i-1})}{K_i}$$

$$\overline{M}_i = \overline{M}_{i-1} + \frac{(M_i) - (\overline{M}_{i-1})}{K_i}$$

$$K_i = F|M_i - M_{i-1}|$$

14 Claims, 5 Drawing Figures

PULMONARY ARTERY PRESSURE

AIRWAY PRESSURE (ESTIMATE)

ARTERIAL PRESSURE $M_i$ = Beat Mean Pressure
$\triangleq \left.\dfrac{\text{Beat Area}}{\text{Beat Time}}\right|_{i\text{ th Beat}}$ Beat-to-beat mean pressure difference

APPARATUS AND METHOD FOR REDUCTION IN RESPIRATION ARTIFACT IN PULMONARY ARTERY PRESSURE MEASUREMENT

BACKGROUND OF THE INVENTION

Whereas the display of a waveform that follows measured variations in bloodpressure can be interpreted by an expert observer with considerable accuracy, there are many situations where it would be far more desirable to indicate each of the systolic, diastolic blood pressures by a single number. In some instruments, the systolic blood pressure is the highest pressure occurring in a five-second interval, but this gives too high a reading in the presence of severe respiratory variation and the readings vary in a way that appear to correlate poorly with the observed waveform. In more recent monitors, systolic and diastolic detectors are synchronized with the EKG and updated at each heartbeat and are slightly filtered. Because the numbers follow the respiration, it is up to the user to make a mental average in order to estimate the true blood pressure. With the advent of microprocessors, various data filtering techniques have been employed, but they have depended on past history in such a way that if they are sufficient to reduce the effects of certain artifacts by a significant amount, their response to sudden changes in actual pressure is too slow. Furthermore, the systolic, diastolic and mean pressures have been processed separately so as to give variations that do not correspond even though they are related to the same factors. Other monitors require the presence of EKG machines or a plethysmograph separation apparatus.

One of the most difficult problems has been to obtain a reliable pressure number under conditions where the blood pressure is highly variable, such as when the pulmonary artery pressure is being measured, because the effects of inspiration and expiration are very great. In this case, the beat-to-beat variation in mean pressure is often greater than the means pressure itself. It is commonly accepted that the best time to read the pulmonary artery pressure is at the end of expiration when the conditions of small and stable airway pressure are most likely to be met. Whereas it is virtually possible to identify the beats taking place during this time, it is not easy to design a monitor that can isolate them. In one approach to this problem, each of the three pressures is treated independently and the weight given to any peak is generally inversely proportional to its deviation from an exponential average. This can result in a pressure that coincidentally is the same as the average being given for too much weight. This and similar methods are completely ineffective when there is little or no pulsation.

BRIEF DESCRIPTION OF THE INVENTION

The essence of one aspect of this invention is illustrated by the expressions set forth below in which $S_i$, $D_i$, $M_i$ respectively represent the maximum minimum and mean pressures of a current heartbeat; $S_{i-1}$, $D_{i-1}$ and $M_{i-1}$ respectively represent the maximum, minimum and mean pressures of the next previous heartbeat; $\overline{S}_i$, $\overline{D}_i$ and $\overline{M}_i$ are weighted values representing the systolic, diastolic and mean pressures to be displayed for the current heartbeat $\overline{S}_{i-1}$, $\overline{D}_{i-1}$ and $\overline{M}_{i-1}$ respectively are weighted values representing the systolic, diastolic and mean pressures of the previous heartbeat and $K_i$ is a function of the absolute difference between $M_i$ and $M_{i-1}$.

$$\overline{S}_i = \overline{S}_{i-1} + \frac{(S_i) - (\overline{S}_{i-1})}{K_i} \quad (1)$$

$$\overline{D}_i = \overline{D}_{i-1} + \frac{(D_i) - (\overline{D}_{i-1})}{K_i} \quad (2)$$

$$\overline{M}_i = \overline{M}_{i-1} + \frac{(M_i) - (\overline{M}_{i-1})}{K_i} \quad (3)$$

$$K_i = F|M_i - M_{i-1}| \quad (4)$$

Of great importance is the fact that the weighting factor $K_i$ is the same for the systolic, diastolic and mean pressures because this causes them to vary in a like manner as one would expect rather than independently of one another.

Whereas the values of $M_i$ and $M_{i-1}$ could be obtained from running averages, an important aspect of the invention is that they respectively be the actual mean pressure of the current beat and the previous beat. Thus, each successive pair of beats controls the weighting factor rather than beats prior to that pair as is the case when the mean pressures are running averages. This means that beats occurring at the end of expiration, i.e., those that are thought to be most representative, will have a much greater effect on all the pressures than other beats because their mean pressures are more nearly the same. The system is more than a mathematical smoothing algorithm because it is intimately tied in with the physiological parameters.

If F is a constant, it has been found that values between 2 and 10 inclusive work very well, but F could be made to vary with beat patterns so as to increase the accuracy of the results obtained.

It is apparent that if the two mean pressures, $M_i$ and $M_{i-1}$, are the same, $K_i$ will be zero and the pressures infinity so that it is well to provide some low limit to $K_i$. A value of 2 has been found satisfactory but other values could be used. A value of 2 implies equal weight for the current beat and the average of the previous beats. On the other hand, if the waveform is very unstable, it is still desirable that it be updated at a reasonable rate so that some upper limit to $K_i$ seems advisable. A value of 30 has been found to work well, but other values could be used.

Another aspect of the invention can be more readily understood by reference to FIG. 1 which shows a pulmonary artery pressure wave and FIG. 2 which shows an arterial pressure wave. In FIG. 1, the pulmonary artery pressure waves seem to be the arithmetic sum of a constant pulse pressure and the airway pressure. The respiratory variation is observed because the transducer is referenced to atmospheric rather than airway pressure. If one were to measure differential pressure between the pulmonary artery and the thoracic cavity, the observed transmural pressure would contain much less of a respiratory component.

This type of respiratory variation is artifact; it results from errors in pressure measurement rather than any fundamental variation in hemodynamic status. The measurement error can be reduced by selecting portions of the waveform where airway pressure is small and relatively stable.

Another form of respiratory variation is shown in FIG. 2. Here we observe a strong dependence of pulse pressure on respiration. At the beginning of expiration, the pulse is small. The pulse builds gradually over the expiratory phase of ventilation. Then, as the ventilator delivers the next beat, the pulse amplitude is seen to decrease.

This effect is seen most easily in arterial pressures rather than pressures on the right side of the heart. Airway pressure appears to modulate rather than add to the blood pressure waveform. Several mechanisms are involved in creating this type of respiratory variation. One is the reduction in venous return to the right atrium when thoracic pressure is raised. Another is reduction in filling volumes due to increased pressure surrounding the heart during the inspiratory phase of mechanical ventilation. The mechanisms are complex, but the net effect appears as modulation of pulse pressure and most likely of stroke volume throughout the respiratory cycle.

Unlike the situation in FIG. 1, these observed changes in the blood pressure waveform are real, not artifactual. The problem is in deciding how to average all the pulses without obscuring the fact that the variation exists, and without compromising response time to significant changes in hemodynamic status.

For these reasons, it has been found highly advantageous to derive pressure by formulae like (1), (2) and (3) except that $K_i$ is a constant rather than a variable. This can be achieved automatically by causing the changes in response to the usual means for setting scale, because it is set lower for arterial pressure measurements than pulmonary artery measurements.

DETAILED DESCRIPTION OF THE INVENTION

Figure 1:
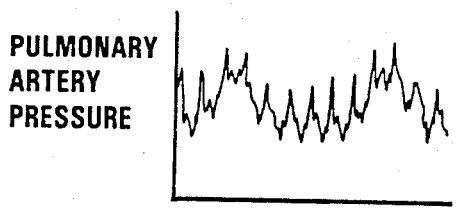
FIG. 1 illustrates a pressure signal derived from the pulmonary artery.
Figure 2:
FIG. 2 illustrates a pressure signal from an artery.
Figure 2:
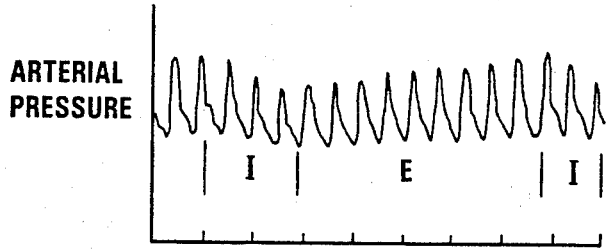
Figure 3A:
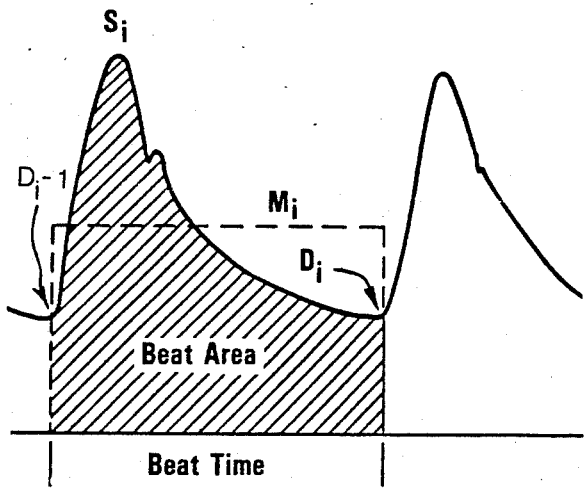
FIG. 3A illustrates the calculation of the mean pressure.
Figure 3B:
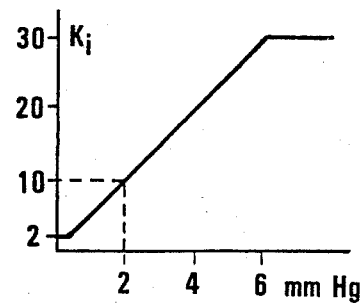
FIG. 3B illustrates a suggested range of values for $K_i$ including the maximum and minimum.
Figure 3:
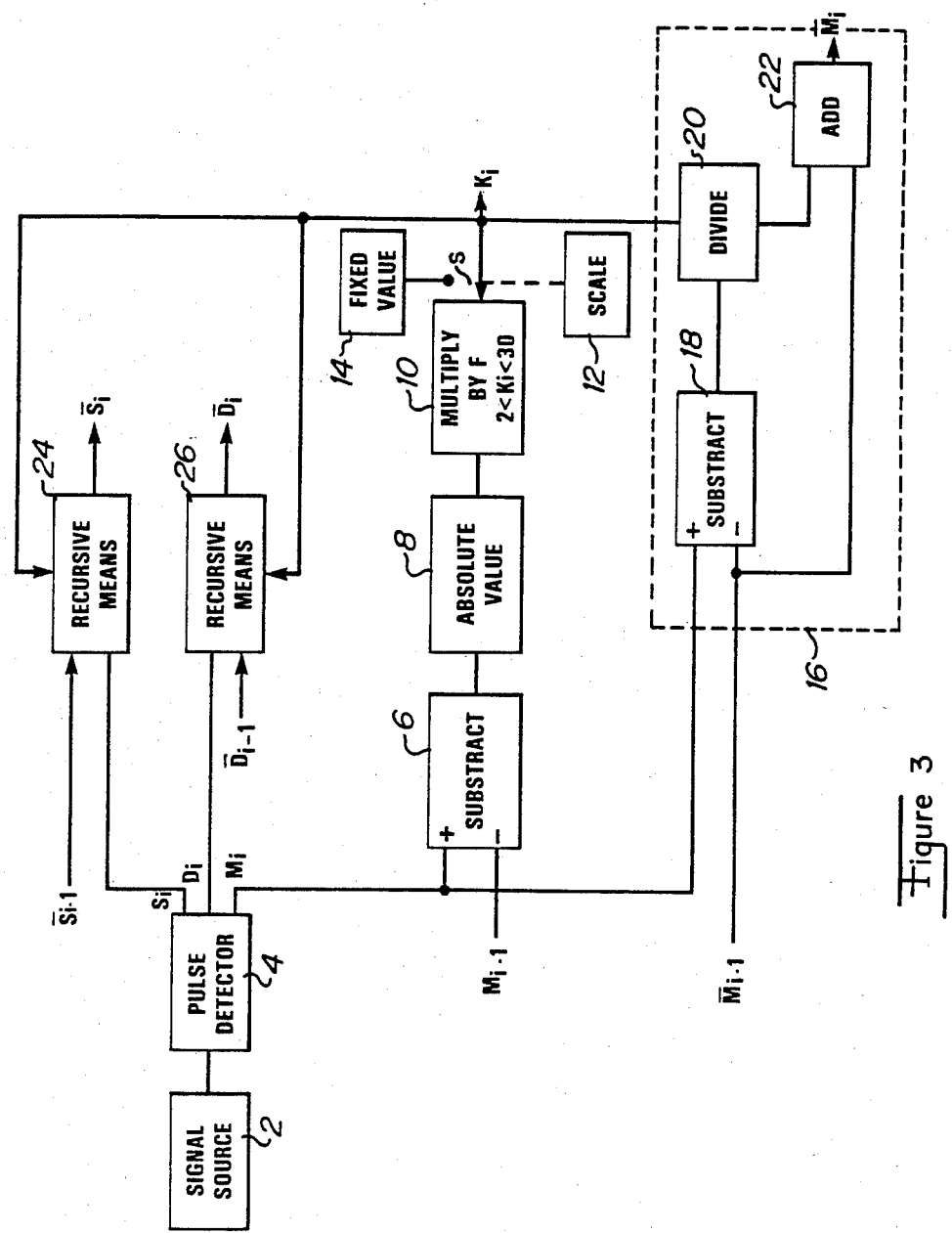
FIG. 3 is a block diagram of a system for displaying values of systolic, diastolic and mean blood pressures in accordance with the invention.

Reference is made to the block diagram of FIG. 3 wherein the signal representing the actual blood pressure variations is provided by a source 2 to any known means 4 for deriving the signals $S_i$, $D_i$ and $M_i$. In the ideal case, the value of $M_i$ is the mean pressure signal $M_i$ between $D_i$ and $D_{i-1}$ as illustrated in FIG. 3A. It and the value of $M_{i-1}$ are applied to a subtracting means 6 so as to derive $M_i - M_{i-1}$. This signal is applied to an absolute value means 8, and its output is applied to a means 10 that multiplies it by a function F which may be a constant between 2 and 10 inclusive, or it may be a variable value. It is suggested that the means 10 limit its output to values between 2 and 30 inclusive. A switch s that is placed in the position shown when a scale selecting means 12 is positioned for the display of pulmonary artery pressure and in its other position so as to derive a fixed value such as 8 from a source 14 when the scale selecting means 12 is positioned for the display of arterial pressure. The output from the switch s is $K_i$. In the first instance, it is variable; and in the second, it is fixed.

The value of $\overline{M}_{i-1} = \overline{M}_{i-1} + (M_i - M_{i-1})/K_i$ is determined by a recursive means 16. The current value $M_i$ is applied to a subtracting means 18 and the weighted output $\overline{M}_i$ of the means 16 for the previous beat, i.e., between $D_{i-2}$ and $D_{i-1}$, is applied to the substracting means 18 so as to be subtracted from $M_i$. This is applied to a divider 20 as a numerator so as to be divided by the value of $K_i$ from the switch s. The quotient provided by the divider 20 is applied to an adder 22 so as to be added to the weighted value $\overline{M}_{i-1}$. Each of the weighted values $\overline{S}_i$ and $\overline{D}_i$ are derived by using recursive means 24 and 26 respectively that operate in the same way as the recursive means 16. The signals $S_i$ and $\overline{S}_{i-1}$ are applied to the recursive means 24 so as to derive the value $\overline{S}_i$, and the signals $D_i$ and $\overline{D}_{i=1}$ are applied to the recursive means 26 so as to derive the value $\overline{D}_i$. The signals $\overline{S}_i$, $\overline{D}_i$ and $\overline{M}_i$ that respectively represent the systolic, diastolic and mean blood pressures for each cycle are displayed in numerical form by a display means 28.

What is claimed is:

1. Apparatus for deriving signals representing the systolic, diastolic and mean pressures of a patient from a signal corresponding to a measured variation in actual pressure, comprising
   means responsive to said signal for providing signals representing successive maximum pressures,
   means responsive to said signal for providing signals representing successive minimum pressures, the portion of the signal between successive minimum pressures defining a beat,
   means responsive to said signal for providing signals representing the mean pressure of each beat,
   means for deriving a weighting factor for each beat that is a function of the absolute difference between the mean pressure of a current beat and the mean pressure of the adjacent previous beat,
   recursive means for deriving a weighted value representing the systolic pressure for the current beat equal to the weighted value representing the systolic pressure of the adjacent previous beat plus the difference between the maximum pressures of the current and previous beats divided by the weighting factor,
   recursive means for deriving a weighted value representing the diastolic pressure for the current beat equal to the weighted value representing the diastolic pressure of the adjacent previous beat plus the difference between the minimum pressures of the current and previous beats divided by the weighting factor,
   recursive means for deriving a weighted value representing the mean pressure for the current beat equal to the weighted value representing the mean pressure of the adjacent previous beat plus the difference between mean pressues of the current and adjacent previous beats divided by the weighting factor, and
   means for displaying said weighted values as the systolic, diastolic and mean pressures for the current beat.

2. Apparatus as set forth in claim 1 wherein the mean pressure is derived by means for integrating the pressure of the said signal occurring between adjacent minimum pressures and dividing said integral by the time interval between these pressures.

3. Apparatus as set forth in claim 1 wherein said function is a constant times the absolute difference between the mean pressure of a current beat and the mean pressure of the adjacent previous beat.

4. Apparatus as set forth in claim 3 wherein said constant is between 2 and 10 inclusive.

5. Apparatus as set forth in claim 1 wherein means are provided for limiting the weighting factor to values between 2 and 30 inclusive.

6. Apparatus as set forth in claim 1 wherein means are provided for substituting a constant for the weighting factor whenever arterial pressure is being measured.

7. Apparatus as set forth in claim 6 wherein said constant is eight.

8. A method for determining the systolic, diastolic and mean pressures for each heartbeat, comprising
deriving a first signal that varies in amplitude in accordance with blood pressure at a given point in the patient's system,
deriving a second signal that successively represents each maximum value of said first signal,
deriving a third signal that successively represents each minimum value of said first signal,
deriving a fourth signal representing a mean pressures occurring in said first signal between successive values of said third signal,
deriving a weighting factor $K_i$ equal to $F|M_i - M_{i-1}|$ wherein F is a function, $M_i$ is the mean pressure of a given heartbeat, and $M_{i-1}$ is the mean pressure of the previous heartbeat,
recursively deriving a weighted signal $\overline{S}_i$ representing the systolic pressure of the given heartbeat which is equal to $$\overline{S}_{i-1} + \frac{(S_i) - (\overline{S}_{i-1})}{K_i}$$

wherein $S_i$ is the maximum value of the first signal occurring during the given heartbeat; $S_{i-1}$ is the maximum value of the first signal occurring during the previous heartbeat; and $\overline{S}_{i-1}$ is the systolic pressure derived for the previous heartbeat,
recursively deriving a signal $\overline{D}_i$ representing the diastolic pressure of the given heartbeat which is equal to $$\overline{D}_{i-1} + \frac{(D_i) - (\overline{D}_{i-1})}{K_i}$$

wherein $D_i$ is the minimum value of the first signal occurring during the given heartbeat; $D_{i-1}$ is the minimum value of the first signal occurring during the previous heartbeat; and $\overline{D}_{i-1}$ is the diastolic pressure derived for the previous heartbeat,
recursively deriving a signal $\overline{M}_i$ representing the mean pressure of the given heartbeat which is equal to $$\overline{M}_{i-1} + \frac{(M_i) - (\overline{M}_{i-1})}{K_i}$$

wherein $M_i$ is the mean pressure of the given heartbeat; $M_{i-1}$ is the mean pressure of the previous heartbeat; and $\overline{M}_{i-1}$ is the mean pressure derived for the previous heartbeat, and
displaying the values of $\overline{S}_i$, $\overline{D}_i$ and $\overline{M}_i$.

9. A method as set forth in claim 8 wherein F is a constant.

10. A method as set forth in claim 8 wherein F is a constant between 2 and 10 inclusive.

11. A method as set forth in claim 8 wherein the weighting factor $K_i$ is limited to values between 2 and 30 inclusive.

12. A method as set forth in claim 8 wherein the weighting factor $K_i$ is set equal to a given constant.

13. A method as set forth in claim 12 wherein said given constant is 8.

14. A method of deriving a signal representing a selected one of the systolic, diastolic and mean pressures of a patient, comprising
deriving an analog signal that varies with the patient's blood pressure at a desired point in his blood circulation system,
deriving first signals respectively representing successive maximum values of said analog signal,
deriving second signals respectively representing successive minimum values of said analog signal,
deriving a third signal respectively representing the mean values of the blood pressure for successive heartbeats,
deriving a weighting factor equal to the absolute value of the difference between the value of said third signal for a current heartbeat and the value of said third signal for the adjacent previous heartbeat times a constant,
deriving the difference between the value of one of said first, second and third signals for the current heartbeat and its value for the adjacent previous heartbeat,
dividing the difference so obtained by the weighting factor, and
adding the result of the division to the weighted value of the adjacent previous heartbeat so as to derive the weighted value of said one signal to be displayed for the current heartbeat.

* * * * *